| United States Patent [19] | [11] Patent Number: 4,929,768 |
|---|---|
| Nakagawa et al. | [45] Date of Patent: May 29, 1990 |

[54] PROCESS FOR PREPARING DIALDEHYDE

[75] Inventors: Sumio Nakagawa, Ogaki; Masaoki Toiyama; Yoshinobu Uno, both of Gifu; Hiromichi Kohda, Hirakata, all of Japan

[73] Assignee: Nippon Gohsei Kagaku Kogyo Kabushiki Kaisha, Osaka, Japan

[21] Appl. No.: 311,253

[22] Filed: Feb. 16, 1989

[30] Foreign Application Priority Data

Feb. 19, 1988 [JP] Japan ................... 63-37782

[51] Int. Cl.$^5$ ............... C07C 45/29; C07C 45/38
[52] U.S. Cl. ................. 568/473; 568/470; 568/471
[58] Field of Search ............ 568/472, 473, 402, 405, 568/471, 470

[56] References Cited

U.S. PATENT DOCUMENTS

| 4,010,208 | 3/1977 | Aicher et al. | 260/603 |
|---|---|---|---|
| 4,219,509 | 8/1980 | Nielsen et al. | 568/473 |
| 4,242,282 | 12/1980 | Diem et al. | 568/471 |
| 4,302,609 | 11/1981 | Baltes et al. | 568/473 |
| 4,359,587 | 11/1982 | Abdurakhmov et al. | 568/402 |
| 4,511,739 | 4/1985 | Sauer et al. | 568/473 |

OTHER PUBLICATIONS

Chemical Abstracts, 23-Aliphatics, vol. 98, 1983, pp. 593.

Chemical Abstracts, 23-Aliphatics, vol. 93, 1980, pp. 599.

*Primary Examiner*—Werren B. Lone
*Attorney, Agent, or Firm*—Armstrong, Nikaido, Marmelstein, Kubovcik & Murray

[57] ABSTRACT

A process for preparing a dialdehyde which comprises subjecting a glycol to oxidation-dehydrogenation in the presence of silver particles of which the surface is partially coated with a silicon carbide powder or a silicon nitride powder. According to the present invention, dialdehydes can be prepared from glycols in high conversion of the glycol in high selectivity into the dialdehyde, and the silver catalyst can be reused even if the reaction is stopped in a while since the silver particles are not aggregated during long time operation.

1 Claim, No Drawings

PROCESS FOR PREPARING DIALDEHYDE

BACKGROUND OF THE INVENTION

The present invention relates to a process for preparing dialdehydes, and more particularly to a process for preparing dialdehydes in high productivity in the presence of a catalyst of silver particles specially prepared to prevent them from aggregation.

There have hitherto been known processes for preparing dialdehydes by subjecting glycols to oxidation-dehydrogenation in the presence of a silver catalyst, as disclosed in, for instance, Japanese Unexamined Patent Publication No. 103809/1979, No. 203024/1982 and No. 59933/1983, and the like. Since the silver catalyst gives higher conversion of glycols and higher selectivity into dialdehydes than other catalysts do, it is most expectd that the silver catalyst be put to practical use in industrial production.

Although the silver catalyst has excellent selectivity, many problems have to be solved until it can be used in practical operation, such that (1) the high selectivity is incompatible with the high conversion, (2) the conversion is lowered due to shrinkage with the passage of time or aggregation of the catalyst, and the like.

When the production of dialdehydes using the silver catalyst is carried out at a higher temperature in expectation to obtain higher conversion, the shrinkage and aggregation of the catalyst further rapidly progress to result in rapid increase in pressure drop and generation of clearance between the reactor wall and a catalyst bed in an early stage of reaction. Thus, once obtained higher conversion quickly deteriorates in short period of time and the catalyst used in such a way can no longer continue efficient reaction and becomes impossible to reuse. In other words, the catalyst of the silver particles has a very short life.

In order to solve the above defects, there are some proposals as to processes, in which a silver catalyst is also used, to prepare formaline from methanol. For instance, it is proposed to use a silver-gold alloy catalyst in Japanese Unexamined Patent Publication No. 112806/1979, but this proposal is not practical from the point of view of the total cost required for raw materials of catalyst and recovery, and the like. Also, Japanese Unexamined Patent Publication No. 133214/1976 proposes a process using silver particles having a specific particle size (0.01 to 10 $\mu$) or a specified range of specific surface area (3 to 30 m$^2$/g), Japanese Unexamined Patent Publication No. 13307/1975 proposes a process wherein silver particles with different particle size are packed in a column to form three or more layers in a certain proportion, Japanese Unexamined Patent Publication No. 33428/1980 proposes a process wherein a net of a metal such as silver or copper is located in a middle of a catalyst layer.

The above proposals in the formaline production process also produce good results in the production of the dialdehydes to a certain extent, but none of them can be substantial solutions to the aforementioned problems. Generally, it is required in commercial plants to start and stop the reaction repeatedly from various operational reasons or troubles. But, by the methods according to the above proposals, if the inner temperature of the reactor decreased to about 300° C. due to interruption of reaction, the catalyst layer is no longer usable because of cracks generated in it and the clearance between the reactor wall. Consequently, it is required to replace the used catalyst with new one. However, it is not easy to take it out from the reactor because the used catalyst is strongly aggregated in the reactor.

An object of the present invention is to provide processes for preparing dialdehydes from glycols in a high conversion of glycols and a high selectivity into dialdehydes, avoiding the above-mentioned problems.

This and other objects of the present invention will become apparent from the description hereinafter.

SUMMARY OF THE INVENTION

It has now been found that when silver particles partially coated with a silicon carbide powder or silicon nitride powder is used as a catalyst in the preparation of dialdehydes from glycols, the problem of cracks, clearance and sintering of catalyst layer can be avoided and eventually there is no significant increase of pressure drop across the catalyst layer for a long period of time of operation. Thus, the new catalyst arrangement exhibits remarkable effects such that the catalyst life is extended considerably, that the conversion of glycols and the selectivity into dialdehydes are maintained at a high level for a long time and that the used catalyst becomes reusable through a simple processing.

According to the present invention, there is provided a process for preparing a dialdehyde which comprises subjecting a glycol to oxidation-dehydrogenation in the presence of silver particles of which the surface is partially coated with a powder of a silicon carbide or a silicon nitride.

DETAILED DESCRIPTION

In the present invention, as a silver catalyst, silver particles are used. Preparation methods of silver particles are not particularly limited and any preparation methods such as a method by electrolysis and a method using an atomizer are applicable to the present invention. There can be practically used silver particles with a particle size of about 5 to 200 mesh, preferably from about 10 to 80 mesh.

In the present invention, it is essential to partially coat the surface of silver particles with the silicon carbide powder or silicon nitride powder. The powder of silicon carbide or silicon nitride with a particle size of 0.01 to 100 $\mu$, preferably from 0.1 to 10 $\mu$, shows remarkabe effect.

As a process for coating the silver particles with the powder of silcon carbide or silicon nitride, it is generally practiced that the silver particles are dry-mixed with the powder of silicon carbide or silicon nitride in a mixer such as a V-shaped blender, and obtained the mixture is heat-treated at a temperature of about 600° to 800° C. to let the silicon powder deposit onto the silver particles. In the present invention, it is necessary to partially coat the silver particles with the silicon powder. It is generally arranged so that the silicon powder covered 1 to 20% of the surface of silver particle and more preferably 5 to 10% of the surface. When the silver particle is completely covered with the silicon powder, it shows poorer catalytic activity.

The silicon carbide or silicon nitride powder is used within a range of an amount of 0.05 to 5.0% by weight, preferably from 0.2 to 2.0% by weight, of the coated silver particle. The silicon carbide powder and the silicon nitride powder may be used alone or as an admixture thereof.

As glycols used as a raw material in the present invention, there are typically exemplified glycols having the formula: $HO-(CH_2)_n-OH$ wherein n is an integer of not less than 2. Typical examples of the glycols are, for instance, ethylene glycol, propylene glycol, 1,4-butanediol, and the like. From ethylene glycol is prepared glyoxal, from propylene glycol is prepared methyl glyoxal and from 1,4-butanediol is prepared 1,4-butanedial (1,2-diformyl ethane).

In the present invention, the oxidation-dehydrogenation reaction is carried out at an elevated temperature in a gaseous phase. The reaction is often carried out within a temperature range of 300° to 700° C., particularly from 550° to 650° C. The reaction is carried out in the vicinity of atmospheric pressure, and, generally, a partial pressure of the raw material, glycol is often not more than 0.5 atm. During the reaction, in order to maintain the partial pressure of the glycol at not more than 0.5 atm, steam, nitrogen, carbon dioxide or the mixture thereof is supplied into the reaction system with the glycol.

In this oxidation-dehydrogenation reaction, oxygen is used as an oxidiger. Oxygen gas and air are often used for such oxygen sources. And, usually as much as 1.1 to 2 times of the stoichiometrical amount to the glycol of oxygen is fed. The contacting time of the reacting mixture with the catalyst is within the range of 0.01 to 1 second, and preferably not more than 0.03 second. In the present invention, it is suitable to adopt a fixed catalyst bed. In case of using fixed catalyst bed, it is preferable that the silver particles are packed into a column so as to form multiple layers with different particle size distribution is located on the side of reaction gas inlet and that with the largest particle size distribution on the side of outlet.

In the present invention, it is not absolutely necessary that the catalyst is of silver particles alone. Copper particles can be used along with the silver particles. In such a case, it is preferable that the copper particles are also partially coated with the powder of silicon carbide or silicon nitride. There is no restriction in using a co-catalyst such as phosphorus or phosphorus-containing compounds to prevent C—C bond in glycols (ethylene glycol, etc.) or dialdehyde (glyoxal, etc.) from fusion.

Dialdehydes thus prepared are chemicals with broad use. They are used in amino acid productions as raw materials. They are also synthesized in various agents for fiber or paper processing, and the like.

In the present invention, when the glycols are subjected to oxidation-dehydrogenation in the presence of the silver particles of which the surface is partially coated with the powder of silicon carbide or silicon nitride, the present invention has great advantage in industrial production of dialdehydes.

The present invention is more specifically described and explained by means of the following Examples, in which all % are by weight unless otherwise noted. It is to be understood that the present invention is not limited to the Examples, and various changes and modifications may be made in the invention without departing from the sprit and scope thereof.

EXAMPLE 1

Silver particles partially coated with silicon carbide powder having different particle sizes were packed in a 20 ml stainless steel tube reactor from bottom to top in order of larger particle size. That is, the group of silver particles having a particle size of from 10 to 20 mesh and 0.2%, based on the coated silver particle, of silicon carbide coating was packed by 3.5 ml at the bottom, the group of silver particles having a particle size of from 20 to 40 mesh and 0.5% of silicon carbide coating was packed by 3.2 ml at the second layer, the group of silver particles having a particle size of from 40 to 50 mesh and 0.5% of silicon carbide coating was packed by 3.2 ml at the third layer, and the group of silver particles having a particle size of from 50 to 80 mesh and 0.5% of silicon carbide coating was packed by 0.8 ml at the top.

After being heated and evaporated, ethylene glycol was mixed with nitrogen gas, air and water (in the state of vapor). Then, the gas mixture was supplied to the catalyst bed which was heated to 400° C. Ethylene glycol was fed at the rate of 160 g/h, nitrogen gas was fed at 700 Nl/h, air was fed at 350 Nl/h, and water was fed at 160 g/h.

The reacted gas mixture taken out from the catalyst bed was introduced to a cold trap cooled with dry ice to obtain a product. In this reaction, the conversion of ethylene glycol was 99.9% and the selectivity into glyoxal was 72%.

After 30 days of continuous reaction, the catalyst bed was carefully examined. No sign of sintering was found in any catalyst layer and the catalyst was taken out from the reactor tube without any trouble and was easily pulverized for reuse.

COMPARATIVE EXAMPLE 1

The procedure of Example 1 was repeated except that no coating was applied to the silver catalyst.

The conversion of ethylene glycol was 98.0% and the selectivity into glyoxal was 68%. After 30 days of reaction, the particles of silver catalyst were severely sintered to form a piece of block. It was not easy to take out the catalyst from the reactor tube, and the used catalyst was no longer usable.

EXAMPLE 2

The procedure of Example 1 was repeated except that silicon nitride was used as a coating material of silver particles instead of silicon carbide.

The conversion of ethylene glycol was 99.9% and the selectivity into glyoxal was 74%. There was no sign of sintering in any layer of the catalyst even after 30 days of continuous reaction.

EXAMPLE 3

The procedure of Example 1 was repeated except that propylene glycol was used instead of ethylene glycol.

The conversion of propylene glycol was 99.8% and the selectivity into methyl glyoxal was 78%. There was no sign of sintering in any layer of catalyst even after 30 days of continuous reaction.

EXAMPLES 4 AND 5

The procedure of Example 1 was repeated except that all of the used silver particles (all of four kinds of silver particles in particle size) have 0.2% of silicon carbide coatings (Example 4), or all of the used silver particles have 1.0% of silicon carbide coatings (Example 5).

The conversion of ethylene glycol was 99.9% in Example 4 and 99.8% in Example 5, and the selectivity into glyoxal was 74% in Example 4 and 70% in Example 5.

COMPARATIVE EXAMPLE 2

Silver particles with different particle size were packed in the same reactor tube as used in Example 1 in order of larger size from bottom to top. That is, the group of silver particles having a particle size of from 10 to 20 mesh and no coating was packed by 3.5 ml at the bottom, the group of silver particles having a particle size of from 20 to 40 mesh and 0.5% of silicon carbide coating was packed by 3.2 ml at the second layer, the group of silver particles having a particle size of from 40 to 50 mesh and 0.5% of silicon carbide coating was packed by 2.0 ml at the third layer, and the group of silver particles having a particle size of from 50 to 80 mesh and no coating was packed by 0.8 ml at the top.

Then, the procedure of Example 1 was repeated. The conversion of ethylene glycol was 99.8% and the selectivity into glyoxal was 70%.

After 30 days of continuous reaction, the catalyst bed was carefully examined. The top layer consisting of the silver particles having no coating was suffered from sintering to form a hard plate. The bottom layer consisting of the silver particles, also, having no coating was suffered from sintering to form an aggregated block. On the other hand, there was no sign of sintering in both the second and third layers consisting of the silver particles having the silicon carbide coating.

In addition to the ingredients used in the Examples, other ingredients can be used in the Examples as set forth in the specification to obtain substantially the same results.

What we claim is:

1. A process for preparing a dialdehyde from a glycol of the formula $HO-(Ch_2)_n-OH$, where n is an integer of not less than 2, comprising subjecting the glycol to oxidation-dehydrogenation in the presence of silver particles having a surface partially coated with a powder selected from the group consisting of a silicone carbide powder and a silicone nitride powder, using oxygen or air as the oxidant, the oxidation-dehydrogenation reaction being conducted at a temperature of 300° to 700° C. and at atmospheric pressure.

* * * * *